United States Patent [19]

Yedgar et al.

[11] Patent Number: 5,064,817

[45] Date of Patent: Nov. 12, 1991

[54] PHOSPHOLIPASE $A_2$ INHIBITING COMPOSITIONS AND THEIR USE

[75] Inventors: Saul Yedgar; Arie Dagan, both of Jerusalem, Israel

[73] Assignee: Yissum Research Development Company of Hebrew University of Jerusalem, Jerusalem, Israel

[21] Appl. No.: 260,588

[22] Filed: Oct. 21, 1988

[30] Foreign Application Priority Data

Oct. 23, 1987 [IL] Israel .................................. 84252

[51] Int. Cl.$^5$ .............................................. A61K 37/64
[52] U.S. Cl. ...................................... 514/78; 514/781
[58] Field of Search ........................ 514/886, 781, 78

[56] References Cited

U.S. PATENT DOCUMENTS 3,959,080 5/1976 Orth ................................... 435/179

OTHER PUBLICATIONS

Blackwell et al., Brt. Med. Bull. (1983), vol. 39, No. 3, pp. 260–264.
Yedgar et al., Febs, vol. 200, No. 1 (1986) pp. 165–168.
Wallach et al., Biochemical Pharmacology (1983), vol. 30, No. 11, pp. 1315–1324.

*Primary Examiner*—John Doll
*Assistant Examiner*—Choon P. Koh
*Attorney, Agent, or Firm*—Millen, White & Zelano

[57] ABSTRACT

Inhibitors of phospholipase $A_2$ activity at the cell-surface membrane whose molecular structure comprises a cell-permeable PLA$_2$-inhibitor moiety covalently bonded directly or indirectly to a physiologically acceptable carrier moiety which is effective to inhibit cell internalization of the cell-permeable PLA$_2$-inhibitor moiety, with the proviso that phosphatidylserine is not bonded indirectly via divalent dodecanedioyl to dextrane hydrazide.

19 Claims, No Drawings

PHOSPHOLIPASE A₂ INHIBITING COMPOSITIONS AND THEIR USE

BACKGROUND OF THE INVENTION

This invention relates to novel compositions of matter which are inhibitors of the enzyme phospholipase $A_2$ ($PLA_2$) at the cell membrane, to methods for their production and to methods for their use to treat $PLA_2$-related abnormal conditions.

Phospholipase $A_2$ ($PLA_2$, EC 3.1.1.4), which hydrolyzes phospholipids at the sn-2 position to produce a fatty acid and a lysophospholipid, is present in almost all cell types and subcellular fractions. See Van den Bosch, H. (1982) "Phospholipids" (Hawthorne, N.J. & Ansell, G.D., Editors), pp. 313-357 (Elsevier Pub., Amsterdam, N.Y.) The activity of this enzyme has been correlated with various cell functions, particularly with secretory processes such as exocytosis and eicosanoid production (prostaglandins, thromboxanes and leukotrienes) See Waite M. (1987) "Phospholipases", Plenum Press, N.Y. Accordingly, $PLA_2$-inhibitors were proposed for treatment of diseases which are associated with enhanced cellular secretion, such as allergy (secretion of hystamine) inflammation (secretion of lysosomal enzymes and peroxides) or thrombosis (secretion of thromboxane)

It is accepted that the enzyme involved in these processes is located in the cell-surface membrane (the plasma membrane), and regulation of the membrane-enzyme's activity is required for regulation of cellular secretion. See Blackwell, G.J. and Flower, R.J. (1983). Br. Med. Bull. 39, 260-264. A number of $PLA_2$ inhibitors have been considered for treatment of oversecretion-related pathological states. Among them are the lipocortin-like proteins which appear in mammalian tissues and assumed to be induced by glucocorticoids (although this has not been unequivocally proven). However, the prolonged administration of steroids has many side effects and, in general, is undesirable. The lipocortin-like proteins can be provided exogenously and might affect the cell membrane $PLA_2$ activity and cellular secretion. However, since these substances are calcium-binding proteins they undesirably interfere with many other cellular functions. See: Crompton et al. (1988) Cell, 55, 1-3.

Other inhibitors, including N-derivatives of phosphotidylserine (see Martina Lagunoff (1982) Biochemistry 21, 1254-1260) are synthetic or natural products of smaller molecular weight which can be administered exogeneously. However, they are also internalized by the cell interfere with the vital lipid metabolism and are therefore cytotoxic. An extracellular inhibitor of $PLA_2$ which affects the enzyme at the cell membrane surface but does not penetrate into the cell would, therefore, be very desirable. The $PLA_2$ inhibitors of this invention fulfill these requirements.

In a paper published in FEBS Lett. (1986) 200 (1), pp. 165-8, which we coauthored with Nurit Reisfeld, we report the synthesis of a cell-impermeable inhibitor of phospholipase $A_2$, by acylating the amino group of phosphatidylserine (PS) with dodecanedioic acid and linking the resulting free carboxyl group to a high molecular weight (70,000) dextran-hydrazide. This inhibitor incorporates into lipid membranes and is capable of blocking the hydrolysis of membrane phospholipids by snake venom as well as by cell membrane $PLA_2$.

This specific $PLA_2$ inhibitor, although cell-impermeable, has been abandoned since dextran-hydrazide is an undesirable moiety from a physiological point of view, and we have since found that linkage of $PLA_2$ inhibiting moieties to other carrier (polymer) moieties produces cell-impermeable $PLA_2$-inhibitors with markedly better properties. These preparations are capable of inhibiting cellular secretion and eicosanoid production, as well as membrane-$PLA_2$ activity in intact cells without impairing the cell viability.

SUMMARY OF THE INVENTION

In a composition aspect, this invention relates to chemical compounds which are inhibitors of the enzyme phospholipase $A_2$ ($PLA_2$) and whose molecular structures comprise a cell-permeable $PLA_2$-inhibitor moiety which interacts with the enzyme at the cell plasma membrane, covalently bonded directly or indirectly to a physiologically acceptable carrier moiety which is effective to inhibit the cellular internalization of the cell permeable $PLA_2$-inhibiting moiety, with the proviso that phosphatidylserine is not bonded indirectly via divalent dodecanedioyl to dextran-hydrazide.

In a method aspect, this invention relates to a method of ameliorating the adverse symptoms exhibited by a living being suffering from a $PLA_2$-related pathological condition, which comprises administering thereto an amount of a compound of this invention effective to ameliorate those symptoms.

In another method aspect, this invention relates to processes for the conversion of a cell-permeable $PLA_2$ inhibitor into impermeable derivatives which are inhibitors of the cell-membrane $PLA_2$ activity.

DETAILED DESCRIPTION OF THE INVENTION

The $PLA_2$ inhibitors of this invention comprise in their molecular structure cell-permeable $PLA_2$ inhibitors, many of which are known in the prior art. The term "moiety" means a chemical entity otherwise corresponding to a chemical compound, which has a valence satisfied by a covalent bond. Typically, the $PLA_2$-inhibitor moiety will be identical in structure to a chemical compound having $PLA_2$-inhibiting activity, except at the point at which that moiety is covalently bonded to the carrier portion of the molecule of the $PLA_2$ inhibitor of this invention, e.g., it differs therefrom by having a valence which replaces a hydrogen atom.

$PLA_2$ inhibitors can be classified into the following types:

I. Phosphatidylethanolamine (PE) and its analogues, such as distearoyl-PE (which gave the best results). Natural PEs from various sources, semisynthetic PEs, synthetic natural and artifactual (novel, unnatural) PEs and their isomers. Any of the above-mentioned compounds linked through the amino group of the ethanolamine by a covalent bond.

II. N-methyl-PE derivatives and their analogues, linked through the amino group of the N-methyl-PE by a covalent bond.

III. N,N-dimethyl-PE derivatives and their analogues linked through the amino group of the N,N-dimethyl-PE by a covalent bond.

IV. Phosphatidylserine (PS) and its analogues, such as palmitoyl-stearoyl-PS (which gave the best results). Natural PSs from various sources, semisynthetic PSs, synthetic natural and artifactual PSs and their isomers.

Any of the above-mentioned compounds linked through the PS amino group by a covalent bond.

V. Glycerol ether, amine, amide, thioether, ester and thioester derivatives of the general formula

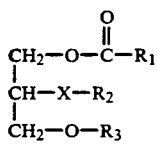

wherein X is -O-, -S-,

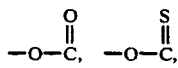

-NH-,

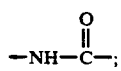

$R_1$ is alkyl, alkyl-COOH, alkylamine; $R_2$ is alkyl, alkyl-COOH, alkylamine, $R_3$ is alkyl, phosphate, phosophorylchlorine, phosphorylserine, phosphorylglycerol, phosphorylinositol, etc., linked to a carrier via one (or more) of the R groups. Best results were obtained with the following compound:

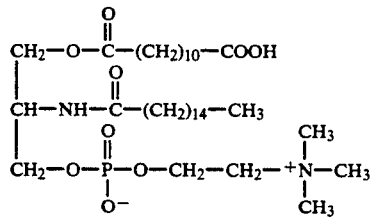

VI. Ethylene glycol derivatives of the general formula

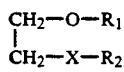

linked to a carrier via one of the R groups, wherein $R_1$ is alkyl,

phosphorylcholine, phosphoryl-serine, phosphorylethanolamine, phosphorylglycerol, phosphonylinositol, phosphate, etc.; R2 is alkyl, alkyl-COOH, alkylamine; X is -O-, -S-,

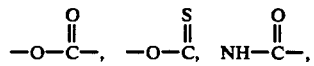

-NH-.

Best results were obtained with the following:

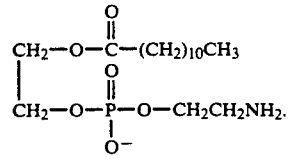

VII. Aminopiperazine and its derivatives.

VIII. Manoalide and its derivatives, synthetic and natural, e.g., manoalogue.

IX. Arachidonic acid and its derivatives, natural and synthetic.

X. p-methoxyphentylamine, its analogues and derivatives.

XI. Sphingosines, their analogues and derivatives.

XII. Phenacylbromides.

Examples of cell-penetrating $PLA_2$ inhibitors which can be employed as the $PLA_2$-inhibitor moiety of the compounds of this invention are aminophospholipids, (e.g., phosphatidylethanolamine, phosphatidylserine), mepacrine, local anesthetics, e.g., chlorpromazine, procaine, indomethacin, sulfated analogs of indomethacin, bromophenacyl bromide, p-methoxyphenethylamine, imipramine, propranolol, phenothiazines, quinacrine, dibucaine, tetracaine, lidocaine, 1-amino-4-octylpiperazine, 1,7-bis(p-aminophenoxy)heptane, tripelennamine, amantadine and phentermine, manoalide, manoalogue, sphingosine and derivatives of each of the above which possess $PLA_2$ inhibiting activity.

The primary role of the carrier moiety is to increase the size (molecular volume) of the $PLA_2$ inhibitor forming the $PLA_2$-inhibitor moiety of the composition of this invention sufficient to render the latter cell-impermeable. When the starting carrier molecule has a substituent which is or can be rendered reactive to a substituent on the starting $PLA_2$inhibitor compound, the carrier molecule can be linked directly to the $PLA_2$-inhibitor molecule. When it does not, a bifunctional linking starting material can be used to link the two molecules together indirectly.

Examples of carrier moieties which can be employed to eliminate the cell-penetrating ability of the $PLA_2$-inhibitor portion (moiety) of this invention are physiologically acceptable polymers, including water-dispersible or -soluble polymers of various molecular weights and diverse chemical types, mainly plasma expanders and food and drug additives, including "Hemaccell" (degraded gelatin polypeptide crosslinked via urea bridges, produced by "Behring") "hydroxyethylstarch" (HES) polyamino acids, hydrocarbon polymers (e.g., polyethylene), polystyrenes, polyesters, polyamides, polyethylene oxides (e.g., polyethyleneglycols), polyvinylpyrrolidones, polysaccharides, soluble cellulose derivatives (e.g., methylcellulose, carboxymethyl cellulose), alginates, assimilable gums (e.g., xanthan gum, stractan), peptides, injectable blood proteins (e.g., serum albumin), cyclodextrin, and derivatives thereof.

The carriers can have a wide range of molecular weight, e.g., above 50,000 (up to a few hundred thousands) when it is desirable to retain the $DLA_2$ inhibitor in the vascular system and below 50,000 when targeting to extravascular systems is desirable. The sole limitation on the molecular weight and the chemical structure of the carrier moiety is that it does not destroy the $PLA_2$-inhibiting activity of the $PLA_2$-inhibiting moiety and does not promote cellular uptake of the $PLA_2$ inhibitor.

Examples of suitable divalent groups forming the optional bridging group are straight- or branched-chain alkylene, e.g., of 2 or more, preferably 4 to 18 carbon atoms, —CO—alkylene—CO, —NH—alkylene—NH—, —CO—alkylene—NH—, cycloalkylene, wherein alkylene in each instance, is straight or branched chain and contains 2 or more, preferably 2 to 18 carbon atoms in the chain, $\text{-(O-ethylene-)}_x\text{O-}$ and $\text{-(O-CH(CH}_3\text{)CH}_2\text{-)}_x\text{O-}$ wherein x is an integer of 1 or more.

Illustrative of compounds of this invention are those in which a PLA$_2$-inhibitor moiety listed below is linked directly or indirectly through a bridging moiety listed below, to a carrier moiety listed below.

| PLA$_2$-Inhibitor Moiety | Bridging Moiety | Carrier Moiety (MW) |
|---|---|---|
| N-derivatized-phosphatidyl-ethanolamines | aminoacids | "Hemccells" |
| N-derivatized-phosphatidyl-serine | diaminoalkyls | carboxymethyl-cellulose |
| Glycerol-ethers and thioethers | diacylcarboxylic acids | methylcelluloses |
| Glycerol-amines and amides | dialcohols dimercaptans | alginates hydroxyethyl starch |
| Glycerol esters and thioesters | dialdehydes | polyethylenes |
| Ethylene glycol derivatives | formylcarboxylic acids | dextrans |
| Retinoides | | albumins |
| Manoalide, manoaloge and their deriatives | | cyclodextrins |
| Arachidonic acid | | polyamino acids |
| Methoxyphenetylamines | | |
| Sphingosines | | |
| Phenacylbromides | | |
| Aminopiperazines | | |

In addition to the compounds of the Examples, further illustrative compounds of this invention are set forth in the table below.

CMC-PS; CMS-PE;
Hemaccell-PS; Hemaccell-PE (Hemaccell M.W.=35,000);
Alginic-PS; Alginic-PE;
Manoalide-Hemaccell;
Manoalogue-dextran (MN 40,000);
p-bromophenacylbromide-Hemaccell;
glycerolether-Hemaccell;
Methoxyphentylamine-CMC;
Methoxyphentylam-HES;
Arachidonic acid-Hemaccell; and
Arachidonic acid-PEG.

PE-phosphatidylethanolamine
PS-phosphatidylserine
CMC=carboxymethylcellulose (M.W. 25,000)
HES=hydroxyethyl-starch (M.W. =40,000)
PEG=polyethyleneglycol (M.W. 4000)

Cell-impermeable PLA$_2$ inhibitors of this invention are prepared by linking a carrier, e.g., a polymer, directly or indirectly to a cell-permeable PLA$_2$ inhibitor according to the general reaction schemes:

a) inhibitor+spacer→inhibitor-spacer+polymer→inhibitor-spacer-carrier b) inhibitor+carrier→inhibitor-carrier c) carrier+spacer→carrier-spacer+inhibitor→carrier-spacer-inhibitor d) inhibitor+reactive group→inhibitor-reactive group+spacer→inhibitor-reactive group-spacer +carrier→Inhibitor-reactive group-spacer-carrier e) carrier+reactive group→carrier-reactive group+spacer→carrier-reactive group-spacer+inhibitor→carrier-reactive group-spacer-inhibitor.

f) inhibitor+reactive group→inhibitor-reactive group
carrier+reactive group→carrier-reactive group
inhibitor-reactive group+carrier-reactive group spacer→inhibitor-reactive group-spacer-reactive group-carrier.

With acylated phosphatidylethanolamine (PE) used as precursor for the PLA$_2$ inhibitor, various lengths of dicarboxylic acids can be used as spacers. These acids can be linked to natural, semi-synthetic or synthetic PE. For example, PE can be linked to aminodextran indirectly as follows:

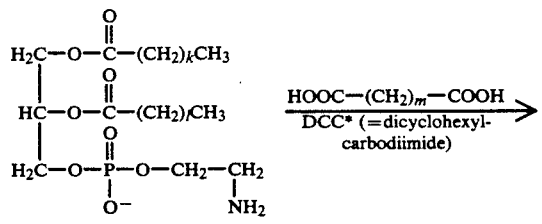

Ia

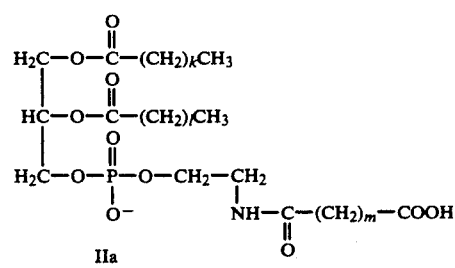

IIa

-continued
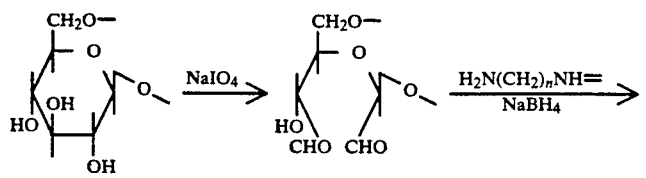
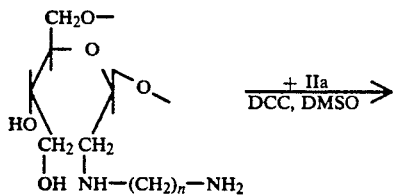
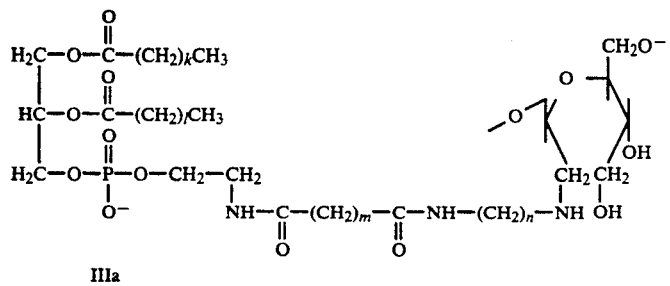
IIIa
Polymers with carboxylic groups, such as polyamino acids, carboxymethyl cellulose or polymers to which fatty acids have been linked, can be linked directly to PE according to the following scheme:
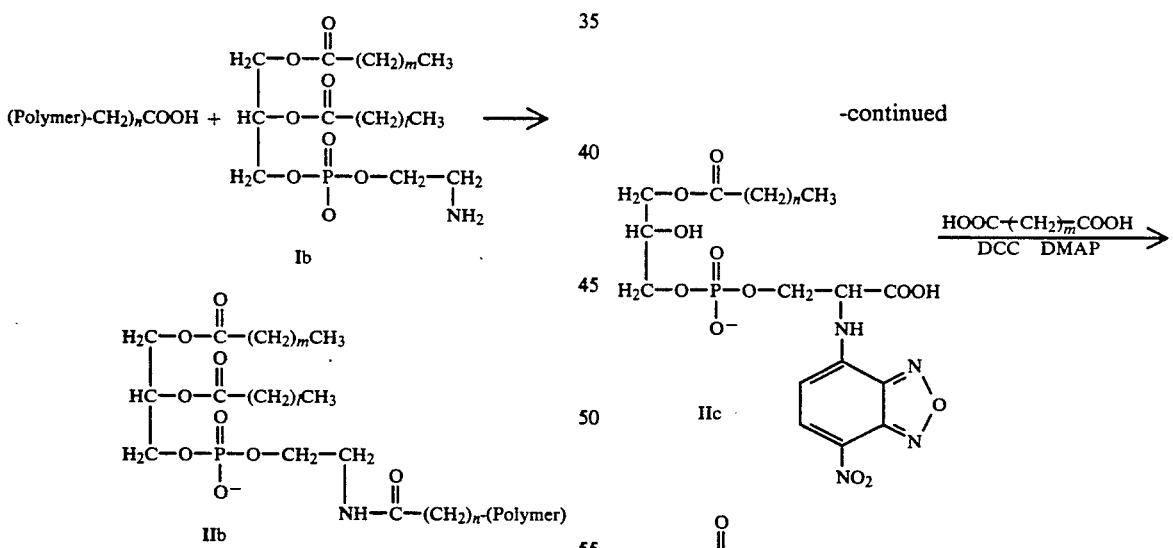
NBD lyso PS can be linked to an amino polymer according to the following scheme:
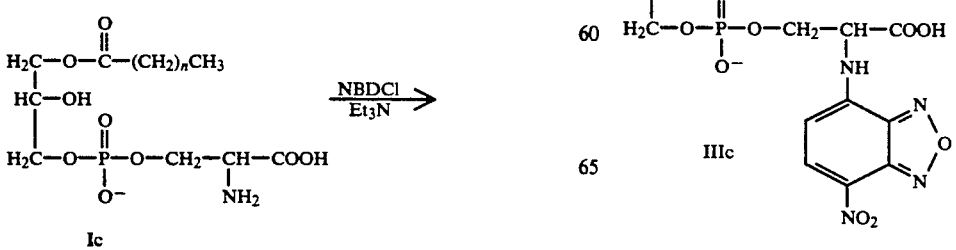

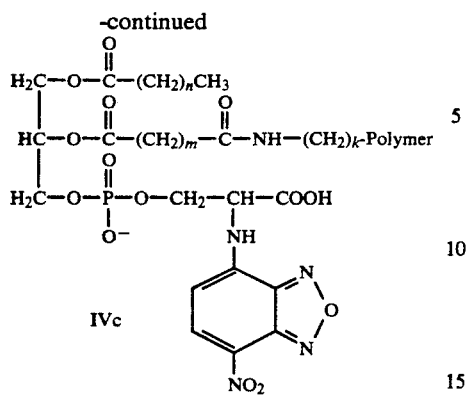

IVc

Glycerol ether, amine, amide, thioether, ester and thioester derivatives of the general formula:

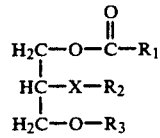

wherein X is —O—, —S-13 ,

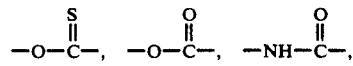

—NH—; $R_1$ is alkyl; $R_2$ is alkyl; and $R_3$ is alkyl,

phosphoryl-choline, phosphoryl-serine, phosphoryl-ethanolamine, phosphoryl-glycerol, phosphoryl inositol, etc., can be linked to the carrier moiety via the R group according to the following reaction scheme:

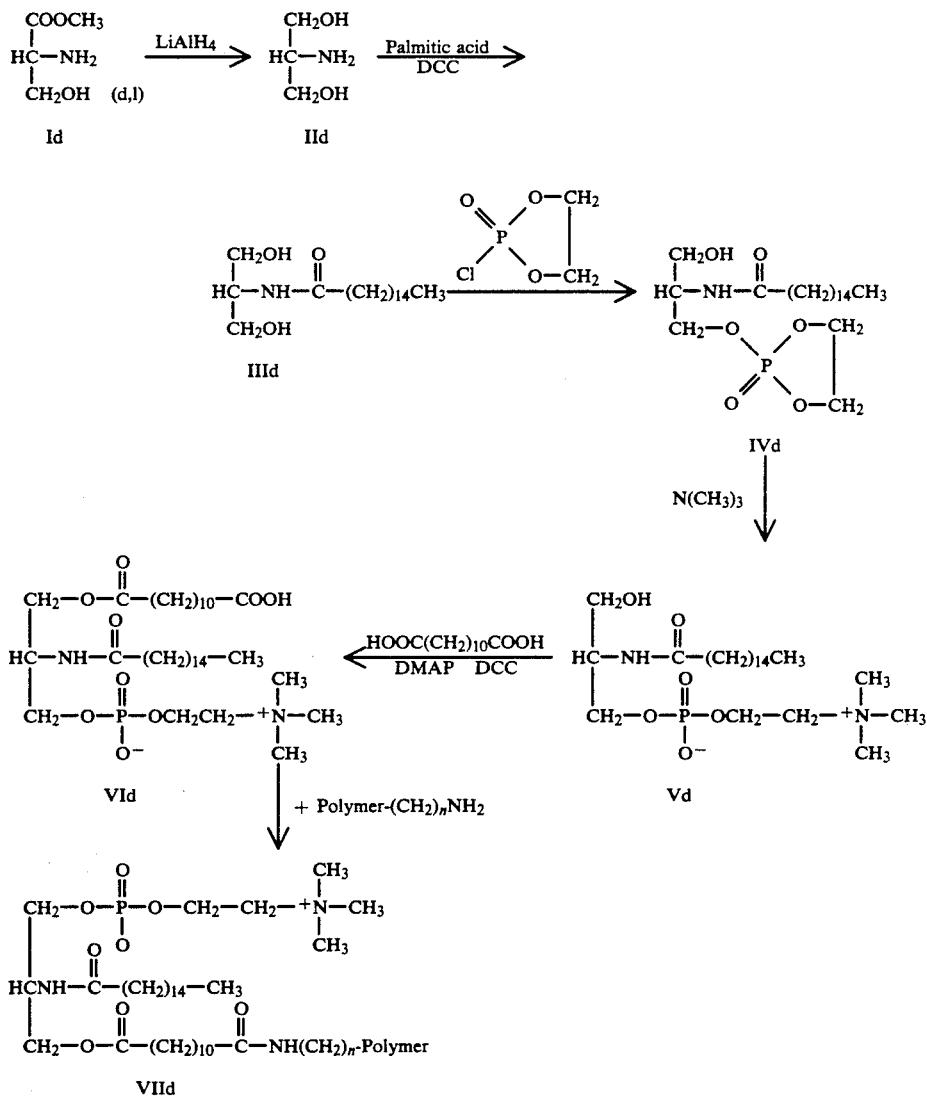

Ethylene glycol derivatives of the general formula:

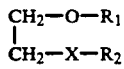

wherein $R_1$=alkyl,

phosphoryl-choline, phosphoryl-serine, phosphoryl-ethanolamine, phosphoryl-glycerol, or phosphorylinositol, etc., and X is —O—, —S—,

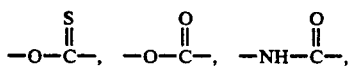

—NH—can be linked to carriers, e.g., by the following reaction scheme, which is an example of the preparation of ethylene glycol monoether phosphatidyl compounds of this invention:

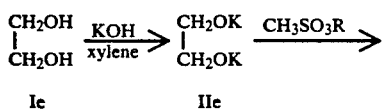

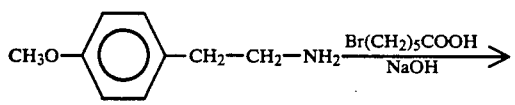

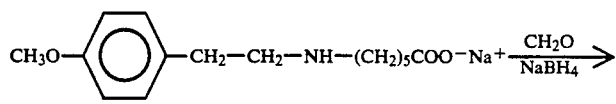

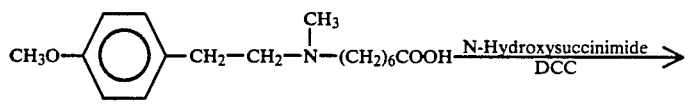

Derivatives of p-methoxyphenetylamine can be bound to a carrier molecule, e.g., dextramine, according to this invention as follows:

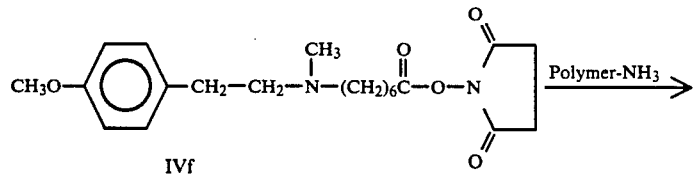

Uses of PLA$_2$ Inhibitors of this Invention

PLA$_2$ is present in animal venom, e.g., of snakes and other venomous reptiles, and in the toxin injected by insect stings, e.g., of bees. The hemolysis and neurotoxicity induced by snake bites and insect stings is mediated by the action of this enzyme on cell surface phospholipids. The PLA$_2$ inhibitors of this invention are therefore useful for the treatment of venom toxicity.

The inhibitors of cell surface PLA$_2$ of this invention can also be used for treatment of diseases associated with excessive endogenous or exogenous PLA$_2$ activity, e.g., in the form of pharmaceutical compositions adapted for such treatment.

The novel extra-cellular inhibitors of this invention comprise a PLA$_2$ inhibitor linked directly or via a suitable spacer to a carrier, the latter generally but not necessarily being a high-molecular-weight substance, such as a polymer. The products of the invention act as extra-cellular inhibitors of PLA$_2$ and thus do not exhibit the cytotoxic effects of PLA$_2$ inhibitors which penetrate into the cells.

The preferred inhibitors of this invention are phosphalidylethanolamine and phosphatidylserine linked directly to or via a divalent bridging moiety to a carrier.

The novel compositions of the invention are useful for the treatment of a wide variety of PLA$_2$-associated conditions, as described hereinafter.

The activity of PLA$_2$ in cell surface membranes has been correlated with cellular secretion in general. Examples of such cell-secreted entities are neurotransmitters, histamine, prostaglandins, leukotrienes, thromboxanes, cholesterol, triglycerides, peroxides, lysosomal enzymes, and secretory products in general. Of special interest are the eicosanoids (prostaglandins, thromboxanes and leukotrienes) which are metabolites of arachidonic acid released from phospholipids by the action of PLA$_2$. Regulation of PLA$_2$ in cell surface membranes thus provides a treatment for pathological conditions associated with oversecretion of these substances, such as occurs in allergic response, inflammation, atherosclerosis, thrombosis, myocardial infarct, hypertension, and neurological disorders, among others, and ameliorating the adverse symptoms associated therewith.

The compounds of this invention have been found to possess the valuable pharmacological properties of the PLA$_2$ inhibitor moiety thereof but lack the side effects thereof associated with cell penetration thereby.

The compounds are particularly useful as anti-inflammatory agents, in the treatment of allergies and oversecretion-related diseases in general. They can be employed in admixture with other drugs indicated for the particular condition being treated.

The compounds of this invention are generally administered to animals, including but not limited to mammals, e.g., livestock, household pets, humans, cattle, cats, dogs, poultry, etc. The pharmacologically active compounds of this invention can be processed in accordance with conventional methods of galenic pharmacy to produce medicinal agents adapted for administration to patients suffering from a PLA$_2$ associated abnormal condition.

The compounds of this invention can be employed in admixture with conventional excipients, i.e., pharmaceutically acceptable organic or inorganic carrier substances suitable for parenteral, enteral (e.g., oral) or topical application which do not deleteriously react with the active compounds. Suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. They can also be combined where desired with other active agents, e.g., vitamins.

For parenteral application, particularly suitable are injectable, sterile solutions, preferably oily or aqueous solutions, as well as suspensions, emulsions, or implants, including suppositories. Ampoules are convenient unit dosages.

For enteral application, particularly suitable are tablets, dragees, liquids, drops, suppositories, or capsules. A syrup, elixir, or the like can be used when a sweetened vehicle is employed.

Sustained or directed release compositions can be formulated, e.g., liposomes or those wherein the active compound is protected with differentially degradable coatings, e.g., by microencapsulation, multiple coatings, etc. It is also possible to freeze-dry the new compounds and use the lyophilizates obtained, for example, for the preparation of products for injection.

Generally, the compounds of this invention are dispensed in unit dosage form comprising 1 to 1,000 mg per unit dosage in a pharmaceutically acceptable carrier.

The dosage of the compounds according to this invention generally is 0.1 to 100, preferably 1 to 20 mg/kg/day, when administered to patients, e.g., humans, to treat, e.g., subcutaneously to treat arthritis, analogously to the known agent, dexamethasone.

It will be appreciated that the actual preferred amounts of active compound in a specific case will vary according to the specific compound being utilized, the particular compositions formulated, the mode of application, and the particular situs and organism being treated. Dosages for a given host can be determined using conventional considerations, e.g., by customary comparison of the differential activities of the subject compounds and of a known agent, e.g., by means of an appropriate, conventional pharmacological protocol.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below are hereby incorporated by reference.

EXAMPLE 1

PVA-PE (a) Preparation of phosphatidylethanolamine (PE) dodecandioic derivative 300 μmol of dodecandioic acid were added to 25 umol of PE dissolved in 2 ml of dry dichloromethane, followed by 100 mg of dicyclohexyl-carbodiimide (DCC), 0.2 ml of triethylamine and 0.5 ml of absolute methanol. The mixture was incubated for 24 hours at 40° C. Analysis of the products by thin layer chromatography, in chloroform:methanol:acetone:acetic acid:-water (3:1:4:0.5), showed two spots sensitive to phosphate spray, identified as PE, near the origin, and Ac-PE at Rf=0.85. This system was used for purification of Ac-PE on silica gel column.

(b) Binding of PVA to dodecandioyl-PE 200 mg EDCC (1-ethy-3-dimethyaminopropyl)-carbodiimide were added to 10 umol of Ac-PS and 50 mg of PVA-hydrazide in 0.5 ml DMSO followed by addition of 200 mg EDCC and stirred for 7 h at 45° C. The PVA conjugate was precipitated and repeatedly washed with ethanol to remove the DMSO and the EDCC. The precipitate was dissolved in 4 ml distilled water, extensively dialyzed against water and lyophilized.

EXAMPLE 2

Dextranamide-PE

Preparation of dextranamine 10 g of dextran-40, MW 40,000, were dissolved in 40 ml of water and oxidized with 0.6 g of sodium periodate during 2 h of stirring with a magnetic stirrer. Thereafter, the oxidized dextran was eluted through a column of 100 ml Dowex 1X8-100 (chloride form) with distilled water. The solution of oxidized dextran was mixed with (5 g) diamino hexane for 1 h, then the schiff base formed was reduced by sodium borohydride 50 mmol. After 5 h of stirring, the conjugate was precipitated with ethanol redissolved in distilled $H_2O$, dialyzed against water and lyophilized.

Preparation of dextranamine dodecanoyl PE

10 $\mu$mol of acetyl-PE, prepared as in Example 1, were reacted with 50 mg of dextranamine in 100 ml DMSO and 200 mg DCC; the mixture Was stirred for 7 h at 45° and the conjugate was precipitated with EtOH washed With EtOH, then redissolved in distilled $H_2O$, dialyzed extensively against $H_2O$, and lyophilized.

EXAMPLE 3

CMC-Acyl-PE

10 $\mu$mole PE were dissolved in 2 ml DMSO and reacted with 50 umol succinic acid in the presence of 500 mg DCC during 2h at 50° C. The carboxyacyl PE formed, was purified on a silica acid column and reacted with 500 mg diaminohexane in 5 ml of chloroform:methanol/1:1, in the presence of 500 mg DCC. The resulted amino derivative of PE was directly coupled to carboxymethylcellulose (CMC, sigma C-8758), by reacting the acyl-PE with 1 g of CMC in 10 ml $H_2O$ in the presence of 200 mg 1-ethyl-3-(-dimethylaminopropyl)-carboxydiimide (EDCC). After an overnight stirring the reaction mixture was dialyzed extensively against $H_2O$ and lyophilized.

EXAMPLE 4

Dextran-PE

Purified carboxy-dextran, prepared by dissolving 10 g of dextran 70 in 40 ml of water and oxidizing and then purifying dextran as described in Example 2, was reacted with 2 g of aminohexanoic acid for 2 hours in $H_2O$, 100 mole of $NaBH_4$ were added gradually over a 2-hour period and then left to stir for another 3 h. 2 ml of EtOH were then added and the solution was left to stir another hour. The reaction product then was precipitated from the reaction mixture with EtOH, washed with EtOH, dissolved in $H_2O$, dialyzed against $H_2O$ and then lyophilized.

The lyophilized carboxy-dextran was dissolved in DMSO and 50 mg thereof in 2 ml and 10 M of PE were added followed by 100 mg of DCC. After 5 hours incubation at 50° C., the dextran-PE was precipitated with EtOH, washed with EtOH, dissolved in water, dialyzed and lyophilized.

EXAMPLE 5

CMC-PE 1 gr of carboxymethyl cellulose (low viscosity Sigma C-8758) was dissolved in 50 ml of $H_2O$. 200 mg of phosphatidyl ethanolamine (PE) was added, followed by 500 mg of 1-ethyl-3-(3-dimethylaminopropyl)carbodiimide. The solution was stirred overnight, dialyzed thoroughly against $H_2O$ and then lyophilized.

EXAMPLE 6

Poly-D-glutamic acid-PE 50 mg poly-D-glutamic acid (MW 50,000–100,000) (Sigma) was reacted with 5 mg of PE in 50 mM phosphate buffer pH 5.2 in the presence of 100 mg of 1-ethyl-3-(3-dimethyl-aminopropyl)carbodiimide. After 5 hours at 45°, the solution was dialyzed extensively against distilled water and lyophilized.

EXAMPLE 7

Polyacrylic acid PE

The reaction was performed as in Example 5, except 50 mg of polyacrylic acid (MW 90,000 or 5,000) were used as the starting polymer.

EXAMPLE 8

NBD-PS Linked to Dextranamine via Dodecandioic Acid 20 mg of lyso PS were reacted with 40 mg of NBDCl in 5 ml of 2:1 MeOH:$H_2O$. $Et_3N$ was added until pH - 8.5 was reached and the pH was kept at 8.5 therewith with stirring for 5 hours. Then the mixture was evaporated to dryness in a Rotavapour at 20° C., then applied to a silica gel column, which was eluted with $CH_2Cl_2$, then successively with $CH_2Cl_2$:MeOH (9:1, 8:2 and 7:3), then $CH_2Cl_2$:MeOH:$H_2O$ (75:25:4, 65:35:5 and finally 50:50:8), where the NBD-lyso-PS eluted as an orange band. The solution was evaporated to dryness. The resulted NBD-lyso-PS (10 mg) was reacted with 20 mg of the di-N-hydroxysuccinimide ester of dodecandioic acid in 1 ml DMSO, in the presence of 5 mg dimethylaminopyridine. The resulting orange compound was purified by preparative TLC on silica gel plates and then reacted with aminodextran, prepared as described in Example 2 in DMSO, by the addition of DCC followed by incubation for 3 hours at 50° C.

EXAMPLE 9

Polyethyleneimine-PS 50 mg of polyethyleneimine (MW 20,000) were reacted with 10 $\mu$M PS in DMSO and 100 mg DCC over a 5-hour period at 45°. Thereafter, the solution was dialyzed extensively against $H_2O$ and lyophilized.

EXAMPLE 10

Hydroxyethylstarch-PE 50 g hydroxyethylstarch (HES, Sigma H-6382) were dissolved in 0.2 N NaOH 100 ml, and 2 ml of epichlorohydrin were added. The mixture was stirred for 2 hours at 40° and then was added to a solution of 3 g 1,6diaminohexane in 200 ml of 0.1 N NaOH. The mixture was stirred for 24 hours at 50° and then precipitated with 3 vol of ethanol, redissolved in $H_2O$, dialyzed against $H_2O$ and then lyophilized. The resulting amino-HES was reacted with acyl-PE as in Example 2.

EXAMPLE 11

Hemaccell-linked to 1-dodecanedioate-2-hexadeconyl amidoglyceryl-phosphonylcholine DL-serine methyl ester (Ig) (1 mol) was added dropwise in 250 ml dry THF to a solution of 0.5 mol $LIAlH_4$ in 1000 ml of dry THF under $N_2$ in a 3000 ml round-bottom flask equipped with a magnetic stirrer, a reflux condenser and a dropping funnel. After stirring for 2 h, 100 ml of ethyl acetate were added slowly from the dropping funnel followed by 100 ml methanol, 200 ml $H_2O$ and 200 ml 1N HCl. The THF phase was separated in a separatory funnel and the water phase was extracted 3 times with $CH_2Cl_2$. The combined THF and $CH_2Cl_2$ phases were dried on $MgSO_4$ and evaporated to dryness.

The amino dialcohol (IIg) was acylated by dissolving 0.5 mol of it in 500 ml $CH_2Cl_2$ in presence of 1.0 mol palmitic acid 2.0 mol $Et_3N$ and 4 mols of dicyclohexylcarbodiimide. After 2 hours reflux the solution was filtered and evaporated to dryness. The amide was purified on silicic acid column eluted with $CH_2Cl_2$:MOH mixtures.

The dialcohol amide (IIIg) formed (0.1 mol) was dissolved in 500 ml of anhydrous benzene containing 0.12 mol $Et_3N$ at 0-5° C. 0.075 mol of 2-chloro-2-oxo-1,3,2-oxaphosphalane were added slowly in 100 ml anhydrous benzene. The mixture was stirred for 12 hours under $N_2$ at R.T. then filtered and evaporated to dryness.

The phosphate triester thus formed (IVe) was transferred to a pressure bottle, dissolved in 100 ml anhydrous acetonitrile and 0.2 mol of trimethylamine were added. The bottle was sealed and kept at 70° for 24 h, then cooled and the reaction product was collected by filtration.

The thus-produced phosphoryl choline amido alcohol (Vg) 0.05 mol was acylated in 200 ml dry $CH_2Cl_2$ using 0.1 mol dodecandioic acid and 0.1 mol dimethylaminopyridine and 0.5 mol DCC. The mixture was refluxed for 5 hours then stirred for 2 hours with 100 ml 1 M $Na_2CO_3$. Then the phases were separated and the water phase was extracted with 4:1 $CH_2Cl_2$:MeOH. The combined organic phase was washed with $H_2O$, dried on $MgSO_4$ and evaporated to dryness.

The resulting oil was purified on a silicic acid column to give Compound VIg, which was reacted with Hemaccell by dissolving 10 mmole of VIg in 10 ml $H_2O$ and reacting it with 10 g of Hemaccell by addition of 20 g of EDCC for 5h with stirring. The coupled Hemaccell derivative dialyzed extensively against $H_2O$ and lyophilized.

EXAMPLE 12

Alginic Acid Derivatives of ethylene glycol phosphorylethanolamine 2.5 g powdered KOH were suspended in 100 ml xylene and 5 mmol dry glycerol were added. The mixture was refluxed in a 250 ml round-bottom flask equipped with a Dean-Stark apparatus, a reflux condenser, a dropping funnel and a magnetic stirrer. After 2 hours of reflux, tetradecyl methane sulfonate (5 mmol) dissolved in 20 ml of xylene was added dropwise. The reflux was continued for 5 hours and then 50 ml of xylene were distilled. The mixture was left to cool, water was added and the reaction product was extracted with $CH_2Cl_2$ dried on $MgSO_4$, evaporated to dryness and purified on a silicic acid column.

The ethylene glycol monoether was phosphorylated as in Example 11. The phosphate triester formed was opened as in Example 11 using liquid ammonia instead of trimethylamine.

The resulting phosphoryl ethanolamine derivative was linked to alginic acid by suspending 1 mmol of the derivatized PE in 100 ml $H_2O$ and reacting it with 5 g. of alginic acid. After 30 min of stirring, 2g. of EDCC were added. The mixture was stirred for 12 h, dialyzed extensively against $H_2O$ and lyophilized.

EXAMPLE 13

Dextran - p-methoxyphenethylamine 0.05 mole of p-methoxyphenethylamine was mixed with 0.05 moles of 6-bromohexanoic acid in 40 ml dioxane. 5 ml of 10% NaOH were added through a dropping funnel over a 15-min. period with thorough stirring. The mixture was further stirred for 2 hours, then acidified with HCl and then extracted with $CH_2Cl_2$ The organic layer was washed with $H_2O$, dried over $MgSO_4$ and evaporated to dryness. The product, N-(4-methoxyphenethyl)-aminohexanoic acid (Ih) was crystallized from $CH_3CN$.

Compound Ih was methylated with formaldehyde by adding it to 30 ml of formalin solution, diluted with 30 ml of methanol. The mixture was stirred for 30 min. then 200 mg of $NaBH_4$ were added followed by 3 successive additions of 200 mg $NaBH_4$ every 20 minutes, with continuous stirring. The reaction mixture was stirred overnight and then 50 ml of $H_2O$ and 60 ml of $CH_2Cl_2$ were added. The organic layer was separated, washed twice with 30 ml of $H_2O$, dried over $MgSO_4$ and evaporated to dryness. The resultant product, N-methyl-N-(4-methoxy-phenethyl)-aminohexanoic acid (IIh), was esterified with N-hydroxysuccinimide by reacting 0.1 mole of IIh with 0.5 mole DCC and 0.11 moles of N-hydroxysuccinimide in 50 ml of $CH_2Cl_2$ with stirring for 5 hours at room temperature. The solution was then filtered off and evaporated to dryness. The product, N-hydroxysuccinimide of IIh (IIIh), was crystallized from acetonitrile.

IIIh was conjugated to aminodextran (MW=4000), prepared as in Example 2, by mixing 20 mg of IIIh, 0.5 g of aminodextran dissolved in 10 ml of $H_2O$, and 100 mg of ethyldimethylaminopropylcarbodiimide (EDCC). The mixture was stirred overnight and then precipitated, washed with EtOH, redissolved in $H_2O$ and reprecipitated with EtOH. The thus-produced dextran-bound p-methoxyphenethylamine was dissolved in water, dialyzed extensively against $H_2O$ and lyophilized.

Activity Data

The activity of phospholipase-$A_2$ in the surface membrane of intact cells was determined in various cell types. Among them were endothelial and mast cells, hepatocytes, platelets and oligodendrites. This activity was inhibited with increasing concentration of extracellular inhibitors; (e.g., The activity of $PLA_2$ in the surface membrane of cultured rat hepatocytes was practically blocked at 100 μmg cell protein of bound PS. In parallel, secretion from these cells (e.g., of prostacyclin, thromboxane, histamine, lyososmal enzymes, triglycerides) as well as platelets aggregation was inhibited in correlation with the inhibition of $PLA_2$ activity.

Hydrolysis of liposomal phospholipids, as well as hemolysis of human red blood cells by snake and bee venom, was inhibited by the $PLA_2$ inhibitors.

In vivo inhibition of thrombus formation in rabbits was obtained by I.V. administration of PE bound to dextran, CMC or Hemaccell, to a final PE concentration in plasma of about 200μM. The application of the active substance is by way of injection, oral (coated or not), rectal or aerosol. The dosage is generally about 5–50 mg/kg of body weight.

The following examples illustrate the $PLA_2$-inhibiting activity of the cell impermeable compounds of this invention. Results obtained with dextranhydrazide-PS (Dex-AC-PS) are given for comparison to demonstrate the efficiency of the compounds of this invention.

EXAMPLE 14

Inhibition of Phospholipase $A_2$ from human PMN leukocytes by cell-impermeable inhibitors (PLI) of phospholipase $A_2$ Method The test compound is incubated (37°, 60 min., pH 7.0) with crude phospholipase $A_2$ (extracted from human polymorphonuclear leukocytes), in the presence of $2.5 \times 10^8$ autoclaved E.coli containing 5 nmol phospholipids labelled with [1-$^{14}$C]-oleate, and 0.5 mmol/l $CaCl_2$. The reaction is stopped by extraction with modified Dole reagent. Free oleic acid is separated on a disposable silicic acid (Kieselgel G 100) column and the radioactivity is determined. Percent inhibition is calculated after subtracting a blank (assay mixture without enzyme).

| Results Inhibition of $PLA_2$ from human PMN | |
|---|---|
| PLI-type | $IC_{50}$ (ug/ml) |
| (a) CMS* | 40 |
| (b) HMS+ | 57 |
| (c) Dex-Ac-PS' | 720 |

*CMS = carboxymethylcellulose-phosphatidylserine
HMS = Hemaccell-phosphatidylserine
', Dextran-hydrazide-dodecanedioic-phosphatidylserine

EXAMPLE 15

Inhibition of $PLA_2$-oedema in rats be cell-impermeable inhibitors (PLI) of phospholipase $A_2$ Method By subplantar injection of 200 U $PLA_2$ (ca. 0.3 mg purified phospholipase $A_2$ from porcine pancreas, Boehringer Mannheim) in 100 μl physiological saline into the left hind paw of male or female rats (LEW/TIF, ca. 200 g body weight, 5 animals per group) a localized edema was induced and its intensity was determined plethysmometrically 3 and 5 hours later. Test compounds were suspended in 0.75% methylcellulose and administered i.p. (5 ml/kg) 1 hour prior to the $PLA_2$ injection. The edema-inhibiting effect was expressed as percent inhibition in comparison to vehicle-treated controls.

| Results: Inhibition of $PLA_2$-oedema in rats | | | | |
|---|---|---|---|---|
| PLI type | Dose (mg/kg) | | % Inhibition 3 hours | 5 hours |
| (a) CMS | 1 × | 20 i.p. | 15 | 29 |
| (b) CMS | | 100 i.p. | 51 | 54 |
| (c) HMS | 1 × | 20 i.p. | 36 | 62 |
| (d) HMS | | 100 i.p. | 63 | 80 |
| (e) HME* | 1 × | i.p. | 0 | 0 |
| (f) HME* | | i.p. | 27 | 25 |
| (g) HME* | | i.p. | 53 | 45 |

*HME = Hemaccell-phosphatidylethanolamine

EXAMPLE 16

Inhibition of Prostaglandin ($PGE_2$) and Leukotriene ($LTC_4$) production in mouse Peritoneal Macrophages by cell-impermeable inhibitors (PLI) of phospholipase $A_2$ ($PLA_2$)

Method

Peritoneal cells from NMRI mice were obtained by lavage with Dulbeccos MEM. The cells were washed and plated at $2 \times 10^4$/well in Dulbeccos MEM with FCS in 96-well plates. After 2 hours (or overnight) incubation at 37°, the adherent macrophages were washed 3 times. The medium was replaced by Dulbeccos MEM with lactalbumin hydrolysate. Test compounds were suspended in water. One hour later, the macrophages were stimulated with $10^{-5}$ M phorbol-myristate-acetate. Another 2 hours later, $PGE_2$ and $LTC_4$ were measured int he supernatants by radioimmunoassay. The results are expressed as $IC_{50}$ of $PGE_2$- and $LTC_4$-production. ($IC_{50}$=PLI concentration which inhibits $PGE_2$ or $LTC_4$ production by 50%)

| Results: PLI-$IC_{50}$ concentration for $PGE_2$ and $LTC_4$ production: | | |
|---|---|---|
| PLI type | $IC_{50}$ for $PGE_2$ production (μg/ml) | $IC_{50}$ for $LTC_4$ production (μg/ml) |
| (a) CMS | 100 | 7 |
| (b) CMS | 100 | 19 |
| (c) CMS | >100 | 28 |
| (d) HMS | >100 | 1 |
| (e) HMS | >100 | 10 |
| (f) Dex-Ac-Ps | 300 | 1000 |
| (g) Dex-Ac-Ps | 600 | 400 |

EXAMPLE 17

Inhibition of Serotonin secretion and Phospholioase $A_2$ ($PLA_2$) activity in Rat Basophilic Leukemia (RBL) cells. by cell-impermeable inhibitor (PLI)

A. Inhibition of Serotonin Secretion with HMS

Inhibition of serotonin secretion by cell-impermeable $PLA_2$ inhibitor:

Cultured RBL were incubated with tritiated serotonin ($10^7$ DPM/ml/$10^6$ cell) for 2 hours, then washed. Serotinin secretion was activated in the absence or presence of HMS (1.5 mg/ml) by the addition of the ionophore $A_{23187}$ (0.3 μM) for the desired time. The radioactive serotonin accumulated in the culture medium during the activation period was determined. In the absence of HMS, approximately 1.3 and 1.9 DPM × $10^5$ was excreted in 15 and 30 minutes, respectively, whereas in the presence of the HMS, only about 0.3 DPM × $10^5$ was secreted in each of these time periods.

B. Inhibition of PLA$_2$ Activity with HMS

Cultured RBL cells were incubated with the fluorescent substrate of PLA$_2$ (C$_6$-NBD-PC) as described by Yedgar et al. (1986) FEBS Letters, 200:165–168. After 1 hour of incubation, the cultures were subjected to lipid extraction and determination of C$_6$-NBD-PC hydrolysed as previously described.

Results:

| HMS concentration (mg/ml) | C$_6$-NBD-PC hydrolysed (nmole/mg cell protein-hour) |
|---|---|
| none (control) | 1.42 ± 0.19 |
| 0.5 | 0.37 ± 0.04 |
| 1.5 | 0.11 ± 0.07 |

EXAMPLE 18

Inhibition of human platelet aggregation and Thromboxane (TXB$_2$) secretion by cell-impermeable inhibitors (PLI) of phospholioase A$_2$ Method:

Platelet-rich plasma (PRP) was obtained from human donors by centrifugation. Platelet aggregation at 37° C. and TXB$_2$ secretion were induced by the addition of an aggregating agent (inducer) as indicated in the table below. Platelet aggregation was determined by measurement of the suspension optical density in a double beam aggregometer. Results are expressed as % of the control aggregation obtained by the addition of the inducer in the absence of an inhibitor. TXB$_2$, secretion to the extracellular medium, was determined by radioimmunoassay. When the test PLI was applied, the PRP was incubated with the inhibitor for 10 min at 37° C., prior to induction of aggregation.

INHIBITION OF PLATELET AGGREGATION AND THROMBOXANE (TXB2) SECRETION BY CELL-IMPERMEABLE INHIBITORS (PLI) OF PHOSPHOLIPASE-A2 (PLA2)

| PLI type | Aggregating agent | PLI conc. (mg/ml) | Aggregation (% of control) | TXB2 secreted (ng/ml) |
|---|---|---|---|---|
| HME≠ | ADP (2 μg/ml) | none | 100 | 82 ± 4 |
|  | ADP (2 μg/ml) | 0.70 | 6 | 14 ± 7 |
| HME≠ | Collagen (40 μg/ml) | none | 100 | 42 ± 6 |
| HME≠ | Collagen (40 μg/ml) | 0.85 | 13 | 17 ± 7 |
| HME≠ | Epinephrine (0.8 μg/ml) | none | 100 |  |
| HME≠ | Epinephrine (0.8 μg/ml) | 0.75 | 9 |  |
| ALS** | Epinephrine (0.8 μg/ml) | none | 100 |  |
| ALS** | Epinephrine (0.8 μg/ml) | 1.5 | 5 |  |
| CME+ | Epinephrine (0.8 μg/ml) | none | 100 |  |
| CME+ | Epinephrine (0.8 μg/ml) | 1.5 | 0 |  |
| CMS++ | Epinephrine (0.8 μg/ml) | none | 100 |  |
| CMS++ | Epinephrine (0.8 μg/ml) | 1.5 | 0 |  |
| ALE* | Epinephrine (0.8 μg/ml) | none | 100 |  |
| ALE* | Epinephrine (0.8 μg/ml) | 0.7 | 9 |  |
| HMS≠≠ | Epinephrine (0.8 μg/ml) | none | 100 |  |
| HMS≠≠ | Epinephrine (0.8 μg/ml) | 1.2 | 2 |  |
| Dex-Ac-PS | ADP* (2 μg/ml) | 3.0 | 14 |  |
| Dex-Ac-PS | Epinephrine (0.8 μg/ml) | 6.5 | 19 |  |

*alginic acid - phosphatidylethanolamine
**alginic acid - phosphatidylserine
+carboxymethylcellulose - phosphatidylethanolamine
++carboxymethylcellulose - phosphatidylserine
≠Hemaccell - phosphatidylethanolamine
≠≠Dextran-hydrazide-dodecanedioyl-phosphatidylserine

EXAMPLE 19

Inhibition of prostacyclin production in endothelial cell by cell-impermable PLA$_2$ inhibitors (CMS and HME)

Method: Cultured adrenal capillary endothelial cells were stimulated to produce prostacyclin (6-keto-PGF$_1\alpha$) by bradykinin in the absence and presence of CMS or HME. The prostacyclin, secreted to the culture medium was determined by radioimmunoassay.

EFFECT OF CELL-IMPERMEABLE PLA$_2$ INHIBITORS ON PROSTACYCLIN PRODUCTION BY ENDOTHELIAL CELLS

| Treatment | 6-keto-PFG$_{1\alpha}$ PROD. (PG/10$^{-6}$ Cells) | % Inhibition |
|---|---|---|
| Bradykinin (1 μM) | 201.9 ± 21.6 |  |
| CMS (1 mg/ml) + Bradykinin (1 μM) | 78.7 ± 6.8 | 61 |
| HME (1 mg/ml) + Bradykinin (1 μM) | 36.4 ± 7.2 | 82 |

EXAMPLE 20

Antiinflammatory activity of cell-impermeable PLA$_2$ inhibitors

Two compounds (CMS and HMS) were tested in the adjuvant arthritis model of inflammation. Paw swelling is induced by an injection of Freunds adjuvant into the right hind paw. Systemic inflammation spreads to the controlateral paw within 2 weeks. The compounds were administered subcutaneously from day 3 to day 14 at a dose of 70 mg/kg. By day 14, paw diameter (measured with calipers) was significantly decreased in arthritic animals dosed with HMS and CMS. The noninjected and injected paws of arthritic rats treated with HMS exhibited a decrease in paw swelling of 43% P≦0.01) and 19% (P≦0.01), respectively. CMS decreased noninjected paw swelling 51% (P≦0.005) and injected paw swelling 30% (P≦0.001). There were no gross signs of toxicity over the two week dosing period. No drug treated group lost weight compared to the arthritic controls.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound which is an inhibitor of the enzyme phospholipase $A_2$ ($PLA_2$) and whose molecular structure comprises a cell-permeable $PLA_2$-inhibitor moiety covalently bonded directly or indirectly to a physiologically acceptable carrier moiety which is effective to inhibit cell internalization of the cell-permeable $PLA_2$-inhibitor moiety, with the proviso that the carrier moiety is not dextran hydrazide.

2. A compound of claim 1, wherein the $PLA_2$-inhibitor moiety is phosphatidyl-ethanolamine or phosphatidyl-serine.

3. A compound of claim 1, wherein the $PLA_2$-inhibitor moiety is an acylated phosphatidylethanolamine or acylated phosphatidyl-serine.

4. An inhibitor according to claim 1, wherein the carrier moiety is a polymer.

5. A compound according to claim 4, wherein the polymer is a degraded gelatin polypeptide cross-linked via urea bridges.

6. A compound according to claim 4, wherein the polymer is carboxymethylcellulose.

7. A compound according to claim 4, wherein the polymer is alginic acid, hydroxyethyl starch polyethylene glycol or dextran.

8. A compound according to claim 1, wherein the $PLA_2$-inhibitor moiety is separated from the carrier moiety by a divalent bridging moiety.

9. A compound according to claim 1, wherein the $PLA_2$-inhibitor moiety and the carrier moiety are bonded directly.

10. A pharmaceutical composition comprising, in admixture with a pharmaceutically acceptable carrier, a $PLA_2$-inhibiting amount per unit dosage of a compound of claim 1.

11. A method of ameliorating the adverse symptoms exhibited by a living being suffering from a $PLA_2$-related pathological condition, which comprises administering thereto an amount effective to ameliorate those symptoms of a compound of claim 1 which is an inhibitor of the enzyme phospholipase $A_2$ ($PLA_2$) and whose molecular structure comprises a cell-permeable $PLA_2$-inhibitor moiety covalently bonded directly or indirectly to a physiologically acceptable carrier moiety which is effective to inhibit cell internalization of the cell-permeable $PLA_2$-inhibitor moiety, with the proviso that the carrier moiety is not dextran hydrazide.

12. A pharmaceutical composition according to claim 10, wherein the $PLA_2$-inhibitor moiety is phosphatidyl-ethanolamine, phosphatidyl-serine, acylated-phosphatidyl-ethanolamine or acylated phosphatidyl-serine.

13. A pharmaceutical composition according to claim 10, wherein the $PLA_2$-inhibitor moiety and the carrier moiety are bonded directly.

14. A pharmaceutical composition according to claim 10, wherein the polymer is a degraded gelatin polypeptide cross-linked via urea bridges.

15. A pharmaceutical composition according to claim 10, wherein the $PLA_2$-inhibitor moiety is phosphatidyl-ethanolamine, phosphatidyl-serine, acylated-phosphatidyl-ethanolamine or acylated phosphatidyl-serine; wherein the polymer is a degraded gelatin polypeptide cross-linked via urea bridges; and wherein the $PLA_2$-inhibitor moiety and the carrier moiety are bonded directly.

16. A method according to claim 11, wherein the $PLA_2$-inhibitor moiety is phosphatidyl-ethanolamine, phosphatidyl-serine, acylated-phosphatidyl-ethanolamine or acylated phosphatidyl-serine.

17. A method according to claim 11, wherein the $PLA_2$-inhibitor moiety and the carrier moiety are bonded directly.

18. A method according to claim 11, wherein the polymer is a degraded gelatin polypeptide cross-linked via urea bridges.

19. A method according to claim 11, wherein the $PLA_2$-inhibitor moiety is phosphatidyl-ethanolamine, phosphatidyl-serine, acylated-phosphatidyl-ethanolamine or acylated phosphatidyl-serine; wherein the polymer is a degraded gelatin polypeptide cross-linked via urea bridges; and wherein the $PLA_2$-inhibitor moiety and the carrier moiety are bonded directly.

* * * * *